United States Patent [19]

Silver et al.

[11] 4,199,564

[45] Apr. 22, 1980

[54] FILM-FORMING ALCOHOLIC MICROBICIDAL TEAT DIP AND METHOD OF USE THEREOF

[75] Inventors: Jules Silver, North Franklin; Thomas G. Borrows, East Hampton, both of Conn.

[73] Assignee: Masti-Kure Products Company, Inc., Norwich, Conn.

[21] Appl. No.: 944,863

[22] Filed: Sep. 22, 1978

[51] Int. Cl.$^2$ ............... A61K 31/79; A61K 31/045; A61K 31/74

[52] U.S. Cl. ........................ 424/80; 424/78; 424/81; 424/263; 424/329; 424/343; 424/346; 424/360; 424/361; 424/363

[58] Field of Search .............. 424/80, 78, 343, 81, 424/263, 329, 346, 360, 361, 363

[56] References Cited

U.S. PATENT DOCUMENTS 4,113,854 9/1978 Andrews et al. .................. 424/78

*Primary Examiner*—Sam Rosen
*Attorney, Agent, or Firm*—Murray and Whisenhunt

[57] ABSTRACT

There is provided an antimicrobial animal teat dip tincture composition and method of use thereof. The ingredients of the composition are: a microbicide, water-soluble, lower alkanol, water and lower-alkanol-soluble film-forming polymer, and a water soluble emollient. Mastitis is controlled by applying the composition to the teats of animals, and allowing the composition to dry on the teats to form a film of the polymer containing the emollient. The lower alkanol gives a very rapid and effective kill of microbes on the teats while the emollient will remain on the teats in the polymer film and prevent chapping and drying of the teats. Preferably, the composition also contains a further microbicide which remains in the polymer film and provides a residual long-term mastitis protection. Quaternary ammonia microbicide compounds provide superior results in this regard, as opposed to other conventional microbicides. The ingredients provide a freeze resistant solution.

32 Claims, No Drawings

FILM-FORMING ALCOHOLIC MICROBICIDAL TEAT DIP AND METHOD OF USE THEREOF

The present invention relates to an antimicrobial animal teat dip which contains an alkanol as a fast acting microbicide and to a method of using the same. In a preferred form of the invention, the composition contains a further microbicide. Thus, this composition not only provides an immediate kill of microbes on the teats of animals but provides a residual antimicrobial effect on the teats, which can protect the teats from mastitis infections until the next milking.

BACKGROUND OF THE INVENTION

Mastitis is a common disease, principally caused by known organisms entering the mammary glands through the teat canal. These microbes include common bacteria which may be transmitted in numerous ways, including direct contact with the teats, as well as airborne transmission. Under the circumstances, mastitis occurs with high frequency in environments where the control of such bacterial population is not easily accomplished.

Mastitis is a particularly difficult problem in connection with dairy herds, since the teats of the cows are frequently manipulated for milking purposes, and in between milkings, the cows remain in barns or pasturage, where mastitis causing organisms can easily survive and proliferate. Further, an infected cow can contaminate conventional milking apparatus, stalls, cleaning materials and the like so that mastitis can easily spread through a dairy herd. Mastitis renders the cow unsuitable for commercial milking and, accordingly, a significant incidence of mastitis in a dairy herd can produce a crippling economic effect of the dairy farmer.

Therefore, it is a conventional practice in the dairy industry to protect dairy cows by applying an antimicrobial composition to the teats of the cows. While these compositions are broadly applicable to the teats of all mammals, since the major economic impact of mastitis is in connection with dairy cows, the following description of the invention will be in connection with and will reference the teats of cows, for the sake of conciseness, although it is to be understood that this term is to be construed in the specification and claims as embracing the teats of all mammals.

The providing of an effective and yet safe teat dip has presented considerable problems to the art. Since the teat dip is normally applied to the dairy cow after each milking, i.e. twice daily, it will be appreciated that many microbicides and compositions thereof are too harsh and irritating for repeated use on sensitive teat tissues. Further, the application of the teat dip to the teat allows ample opportunity for the microbicide to contaminate the milk. Thus, it is imperative that the microbicide of the teat dip be "water soluble or dispersible." Thus, the microbicide is easily washed from the teats to prevent contamination of the milk.

In the foregoing regard, U.S. Pat. No. 3,928,556 extensively discusses the irritating sting of polymer containing and bactericide containing liquid wound dressings, which can be used as a wound dressing to protect cows having mastitis on the teats, and suggests solvent systems with major amounts, i.e. at least 50% of non-stinging tert-butyl alcohol, along with minor amounts of stinging alcohols, e.g. lower alkanols and non-stinging hydrocarbon and fluorocarbon solvents. While these wound dressings are non-irritating (stinging is this case), they are not water-soluble and cannot be used as a routine teat dip.

Further, since the cow is most vulnerable to mastitis invasion during milking and immediately thereafter, teat dipping is most effective when performed immediately after milking. This provides protection from the environmental infection sources in the barn and pasture areas. Accordingly, it is highly desirable to provide a fast acting teat dip, since extended times for effectively using the dip will undesirably slow down the overall milking procedure or provide less than required mastitis protection. Thus, a desirable teat dip must be capable of providing an adequate kill of bacteria on the teat in a reasonably short time, e.g. ten minutes or less, since times beyond this period greatly limit the effectiveness of the teat dip.

In view of these exacting requirements, the art has produced only a few economical and effective teat dips. While many microbicides are known which can produce an adequate kill of the microbes in the required time, and even provide some residual effects, the resulting irritation of the teats and the lack of water-solubility or dispersibility reduces the possible candidates for this application most substantially. The teat dip most widely used contains iodine, since the iodine composition is water-soluble and fast acting, but iodine suffers from decided disadvantages. It is substantially irritating to the teats of cows, care must be taken to minimize the contamination of the milk with the toxic iodine, and iodine is a strong oxidizing agent and reacts quickly with most material it contacts. This latter property substantially reduces the residual microbicidal effect. This property also tends to substantially reduce any activity of other microbicides compounded with the teat dip.

U.S. Pat. No. 2,739,922 issued to Shelanski discloses a combination of iodine and polyvinylpyrrilodone and related film-forming polymers. This combination lowers both the acute toxicity and the chronic toxicity of the iodine and reduces the irritation and sensitization effects of iodine. While iodine staining is also mitigated, the combination does not totally obviate the same, and continued topical use will cause permanent staining of the skin. However, iodine and/or iodine-polyvinylpyrrilodone combinations still suffer from the disadvantages of toxicity and the reactivity of the iodine, even in the polyvinylpyrrilodone.

Accordingly, it would be of substantial advantage in the art to provide a teat dip which has a rapid kill of mastitis causing bacteria, can be repeatedly applied, without irritation to the teats, is not toxic, is water-soluble or dispersible, and will not stain or otherwise harm the teats. These properties would provide the advantages of the iodine-type teat dip, but without the disadvantages thereof.

THE OBJECTS OF THE INVENTION

It is therefore an object of the invention to provide an antimicrobial animal teat dip which provides a rapid kill of mastitis causing microbes, is water-soluble, is non-irritating and non-toxic. It is a further object of the invention to provide such compositions whereby a residual amount of the composition on the teats is visually detectable in order to indicate the necessity for reapplication of the teat dip, which function is convenient for ensuring protection of the cows. Finally, it is an object of the invention to provide a method of controlling mastitis in cows with use of the composition of the invention which includes a further active microbicide for providing residual antimicrobial activity. Other objects will be apparent from the disclosure and claims as follow.

BRIEF DESCRIPTION OF THE INVENTION

The invention is based on two primary discoveries. The first discovery is that many microbicides are sufficiently active for long exposure kill of mastitis causing organisms, but are not sufficiently active for rapid kill required in a teat dip. As a subsidiary feature is the further discovery that certain microbicides combine the desired properties of rapid kill of common mastitis causing organisms and have no substantial toxic effects. These microbicides are lower alkanols of 1 to 3 carbon atoms. These will provide a very rapid kill of mastitis causing organisms so as to produce a very initially effective teat dip, but the residual microbicidal effect is minimal. As a subsidiary feature of this discovery is the further discovery that the lower alkanols may be combined with further microbicides, wherein these microbicides are not deactivated and, hence, provide a rapid initial kill and a longer term residual microbicidal effect.

The second basic discovery is that an achieving the effects of the foregoing discovery, irritation of the cow's teats occasioned by the use of a usually stinging lower alkanol, which further removes natural oils from the teats, may be substantially mitigated by including in the teat dip an emollient. As a subsidiary feature of this discovery is the further discovery that the emollient will be held in place on the teats for long term effect by including in the dip a film-forming soluble polymer.

As can be appreciated, in view of the ingredients noted above, it is further necessary that the film-forming polymer be water and lower alkanol-soluble, and that the microbicide and emollient have good storage stability, e.g. upon freezing and thawing the composition is not deactivated, since such conditions may be experienced during storage.

Accordingly, there is provided an antimicrobial animal teat dip tincture composition comprising the ingredients of a microbicidal lower alkanol of 1 to 3 carbon atoms; a non-toxic water and lower alkanol-soluble film-forming polymer; a water-soluble emollient (water-/alkanol soluble); and water; wherein the composition provides a fact acting microbicidal teat dip which does not cause substantial irritation to the teats with repeated use thereof.

There is provided a method for preventing mastitis in the teats of animals comprising applying to the teats that composition and allowing the composition to dry on the teats to form a film of the polymer containing the emollient and microbicide.

Preferably, the composition also contains a water-soluble dye which is contained in the teat dip composition, and resulting polymer film, as visual evidence of teat dip presence or the need thereof.

DETAILED DESCRIPTION OF THE INVENTION

As broadly stated, the present teat dip comprises an ingredient which will effect a rapid kill of mastitis causing organisms. This first ingredient is the lower alkanol. The lower alkanols useful in the present invention as microbicides have 3 carbon atoms or less, and preferably are the saturated lower alkanols, e.g. methanol, ethanol, propanol and isopropanol. It will also be easily appreciated that the lower alkanols combine that antimicrobicidal properties with the high vaporization property. It is with this high vaporization property (alcohol and water) that the liquid will so rapidly leave the applied teat that the polymer film (described hereinafter), with the emollient therein, will form before contamination or loss of residual microbicide occurs.

Lower alkanols are known as good microbicides, but it has now been discovered that they give extremely rapid kill of mastitis causing organisms. However, as is well known, these relatively high vapor pressure alcohols rapidly evaporate from living animal skin and remove moisture from the skin in drying. Further, the natural oils are dissolved out of the skin and the skin is cooled. Thus, these effects form nearly perfect conditions for irritation, stinging, chapping and roughness of the sensitive teats. Further, once these alcohols are removed from the teats by evaporation, little, if any, residual microbicidal effect is provided. Thus, the use of lower alkanols would ordinarily be considered unsatisfactory for teat dips.

It has been discovered that the unsatisfactory effects of the lower alkanols can be mitigated when the teat dip contains a water-soluble emollient. Many emollients of this nature are well known to the art and the particular chemical composition of the emollient is not critical. It is necessary that the emollient have the normal softening effect on the teats without compromising the microbicide. Thus, conventional emollients such as glycerol, sorbitol and water-dispersible lanolin may be used.

The combination of lower alkanol and emollient will allow the use of the lower alkanol for rapid kill of mastitis causing organisms in the teat dip without adversely affecting the teats of the cow, only if that emollient remains on the teats a sufficient length of time to produce a softening effect. To achieve this sustained contact of the emollient with the teat, a non-toxic, water and lower alkanol-soluble film-forming polymer is provided in the composition. After evaporation of the lower alkanol, the remaining emollient is contained in the resulting film, and will keep the emollient in contact with the teat to provide the softening effect.

As a further feature, it has been discovered that film-formers of that nature will substantially slow the evaporation rate of the lower alkanol as well as retard removal of moisture and oils from the teats. As noted, this removal of moisture and oils causes serious irritation, chapping and ultimately, inability for milk production. Under the circumstances, for purposes of the present invention, the film-forming polymer must therefore be water and lower alkanol-soluble. Of course, since the amount of film-former involved will be of a substantial quantity, the film-former must be non-toxic.

Such film-formers are known in the art. However, it has been found that certain groups of such film-formers and advantageous from both an ease of application and effectiveness point of view. Film-formers having these additional properties are vinyl polymers, natural gum polymers and gelatin. Polymers and interpolymers of vinylpyrrilodone, vinylphthalimide, vinylpyridine, vinylcaporlactam, vinylvalerolactam and vinyl alcohol-/acetate are examples of such water-soluble vinyls. Gum acacia, gum carrageenan, gum arabic and the like are examples of natural gums.

It should be understood that the film-forming polymer may be soluble in water and lower alkanol separately but since in use, the film-forming polymer will be dissolved in the combination of water and lower alkanol (a tincture). it is required that it be at least water and alcohol (a tincture) soluble, although often the film-forming polymer will be soluble in each. Thus, the specification and claims should be construed as requiring solubility only in the combination of water and alcohol (a tincture).

It has been discovered that the lower alkanols have yet a further unexpected property. They do not tend to inactivate other microbicides such as is the case with iodine and like microbicides. Thus, the present composition may advantageously contain a further microbicide of a conventional type. Where this further microbicide has residual activity, prolonged mastitis protection is achieved, since this further microbicide will be contained in the dried polymer film on the teats and be resistant to sluffing or washing off the teats of the foraging animal. The particular microbicide is not critical so long as the microbicide is effective against mastitis causing organisms. Thus, suitable microbicides are the phenylic and napthalenic compounds or the heterocyclic derivatives thereof. Preferably, the microbicide is selected from the group consisting of phenol, halogenated phenol, quinolines, resorcinols, chlorinated xylenols, chlorhexidine and pyridines. However, it is to be understood that the further microbicide is not limited to the foregoing, and any of the conventional microbicides which are active against common mastitis causing organisms may be used. In case of any doubt as to the effectiveness of a particular microbicide, the acceptability (activity) thereof can be evaluated according to the procedure of Example I herein. Generally, a reduction of at least one log from the negative control should be achieved, and more preferably at least two logs or at least three logs.

It is preferred that the further microbicide is water and alcohol soluble, since this will allow its solution in the teat dip as described above. In this regard, and as a further important feature of the invention, it has been discovered that a certain class of known microbicides are effective against mastitis causing organisms, and are also water and alcohol-soluble. This class of microbicides is the quaternary ammonia compounds, e.g. cetyl pyridinum chloride, quaternary ammonium compounds with $C_{12}$ to $C_{18}$ alkyl chains, cetyl trimethyl ammonium bromide, benzethonium chloride and N-alkyl-dimethyl benzyl ammonium chloride (alkyl=$C_8$ to $C_{16}$ or mixtures thereof). Of these, cetyl pyridinum chloride in the present composition is as effective as the commercially available iodine containing teat dip composition against common mastitis causing organisms, which is highly unexpected, and is the best mode of the present invention. An equivalent mode of the invention is the use of the N-alkyl-dimethyl benzyl ammonium chloride in that it is essentially as active as the cetyl pyridinum chloride, and is also water/alcohol-soluble.

It will also be appreciated that since the microbicide is contained within the film produced by the film-forming polymer, the presence on the teats of the microbicide will be prolonged, since the film will reduce the rate at which the microbicide will be removed from the teats of the foraging animal. Similarly, the film will provide a therapeutic effect in keeping the emollient in active contact with the teats and providing a weather barrier for healing existing cracked and chapped teats. The residual microbicide will mitigate the chances of skin infection during this healing period.

These effects are significantly different from the effects of the plastics would dressing disclosed in U.S. Pat. No. 3,928,556. While the dressings contain a filmable plastic and lower alkanols, they must contain at least 50% of a higher alcohol, e.g. tert butanol (along with a further microbicide). Thus, no quick kill of mastitis causing organisms is provided, nor is a quickly evaporated alcohol provided, and hence, no quickly established polymer film is provided. However, this is expected since the "wound dressings" perform a different function than the present teat dip.

It will also be appreciated that if the microbicide is not soluble in water and alcohol, a solution will not be formed. Thus, while water and alcohol-insoluble microbicides may be used, e.g. the phenolic microbicides, their use will necessitate the forming of an emulsion of the teat dip composition. To this end, a non-deactivating water and lower alkanol-soluble emulsifier is used. However, as is well known, many surface active agents (emulsifiers) will deactivate microbicides. This is particularly true in regard to non-ionic surface active agents, and the art has long recognized the same. It is, therefore, necessary for the emulsification to be accomplished with a surface active agent which does not cause substantial deactivation of the microbicide. The suitability of any particular emulsifying agent may be tested simply by preparing the emulsion and determining the activity of the microbicide with and without the emulsifier. Reduction in activity should be avoided. This is not a preferred embodiment.

However, generally speaking, suitable emulsifiers are the conventional sulfonated detergents of th formulae R—$SO_3$—M, R—$C_6$—$H_4$—$SO_3$—M and R—O—$SO_3$—M, where R is $C_{12}$ to $C_{18}$ aliphatic hydrocarbons and M is an alkali metal or alkaline earth metal. R may be a branched or straight chain hydrocarbon and may be saturated or unsaturated, but preferably it is a straight chain unsaturated fatty acid residue. Any of the alkali and alkaline earth metals may be used with the sulfonated detergents.

Alternatively, the emulsifiers may be one of the conventional salts of a $C_{12}$ to $C_{20}$ alkyl amine or the quaternary ammonium salt thereof. This class of emulsifiers is well known to the art and need not be described in any detail herein. Polyethylene glycol esters of a $C_{12}$ to $C_{18}$ aliphatic acid may also be used. A similar class of compounds which may used are the esters of the $C_{12}$ to $C_{18}$ alcohols and alkylated phenols or napthols (and the sulfonated derivatives thereof).

A preferred emulsifier is sodium lauryl sulfate, since this emulsifier has been found to have a desirable set of properties. It is essentially non-deactivating, an emulsion can be easily formed, and it will emulsify relatively large proportions of water-insoluble liquids. The emulsions produced can withstand substantial mechanical shock as well as temperatures from just above freezing of the emulsion up to close to the boiling point of the emulsion.

In this latter regard, as can be easily appreciated, if the emulsion is not stable over a relatively wide range of temperatures, the emulsion may accidentally be broken, and application of the teat dip to the teats of the animals would be problematic. Preferably, the emulsion should have the characteristics of being stable over repeated freezing and thawing, since these conditions are likely to be encountered in barn storage.

The proportion of the ingredients can vary widely but the following ranges are generally quite satisfactory. These ranges of proportions of ingredients are on a prepared for immediate use basis. That is to say that the concentrated material, if any, has been diluted to the concentration for immediate use as a teat dip. On this basis, the alcohol should be between about 15% and 70%, more preferably between about 30% and 50%. The film-forming polymer should consistute between 0.1% to about 10% of the composition, more preferably from about 0.5% to 5%. The emollient should be between 0.1% and 10%. The amount of emulsifier, if used, may be quite low, as low as 0.1%, or it may be quite high, up to about 10%. However, usually this will be between 0.5% and 7%. The amount of the further microbicide will vary, of course, with the activity of the particular microbicide, but generally will be between 0.1% and 5%, although more usually this will be between 0.3% and 2.0%. The remainder is water, aside from optional ingredients as described below.

The optional ingredients include a buffering agent, such as a combination of sodium citrate and citric acid to control the pH of the composition between 4 and 7, which is more comfortable for application to the teats. Also, the composition may optionally contain a sequestering agent for preventing precipitation of any of the ingredients in hard water. A typical sequestering agent is ethylene-diamine-triacetic acid (EDTA) in amounts of between 0.1% and 5%, preferably no more than 2%.

Also, optionally, but certainly preferred, the composition may also contain a water-soluble, non-toxic dye, such as any of the conventional FD & C dyes. A particularly suitable dye is Yellow No. 6, and is contained in the composition of less than 2%, so that the yellow color will be visible on the teats of the animal so long as the microbicidal residue is retained on the animal's teats.

Finally, if desired, alcohol drying agents, perfumes, stabilizers, viscosity control agents and the like may be used, all of which will perform their known function.

The invention will now be illustrated by the following Examples, but it is to be understood that the invention is not limited to the Examples but extends to the breadth of the foregoing disclosure and the following claims. In the Examples, as well as in the specification and claims, all percentages and parts are by weight unless otherwise specified.

EXAMPLE I

|  | SAMPLE A % w/v | SAMPLE B % w/v |
| --- | --- | --- |
| CPC (cetyl pyridinum chloride) | 0.50 | 0.50 |
| Triton X-100 (detergent) | 0.2 | 0.2 |
| Sodium Citrate | 0.0053 | 0.0053 |
| Citric Acid | 0.019 | 0.019 |
| FD & C Yellow No. 6 | 0.27 | 0.27 |
| PVP | 0.94 | 0.94 |
| Isopropanol | 31.2 (40% v/v) | 31.2 (40% v/v) |
| Sorbitol | 3.2 | 3.2 |
| Glycerine | 4.5 | 4.5 |
| Nilodor (deodorizer) | 0.0425 | — |
| Water q. s. | 100% | 100% |

The PVP was dissolved in the alcohol and the remaining ingredients were dissolved in water. The alcohol and the water portions were then mixed.

The effectiveness of the teat dip was evaluated by the standard in vitro testing procedure known as the "Excised Teat Procedure" (see Twomey, A. and M. A. Arnold, 1977 Laboratory Technique for Evaluating Test Santicizers for Mastitis Control, N. Z. VET. J.). The organisms used in the test were *Staphylococcus aureus* (ATCC 27543) and *Streptococcus agalactiae* (C 48). In this procedure, excised teats from slaughtered dairy cows are washed in a mild detergent solution, rinsed and dried. The so-prepared teats were dipped in 70% alcohol and dried with a paper towel. The teats were dipped to a depth of 15 mm in the challenge suspension of the test organisms, and allowed to drain for 15 minutes for a control, and 5 minutes for the test teats. The test teats were dipped to a depth of 30 mm in Sample A or Sample B and drained for an additional 10 minutes. Organisms were removed by rinsing each teat with 5 ml. of quencher solution expressed from a polyethylene wash bottle. 5 ml. of the rinse is collected in sterile plastic vials and diluted with 0.1% proteose peptone. Plating is carried out in a conventional manner. As a comparison, the same test is performed with a commercially available iodine teat dip (Bovadine, manufactured by West Chemical Co.). This is considered as a positive control. The teats with only test organisms thereon are considered as a negative control.

The results obtained for *Staphylococcus aureus* were as follows. The negative control showed a log of 6.6 Colony Forming Units (CFU), while the positive control showed a log of 1.27 CFU, and the present teat dip showed a log of 1.39 CFU. The reduction from the control log was, accordingly, 5.33 and 5.21, respectively. This demonstrates the effectiveness of the present teat dip. Similar results were obtained with the *Streptococcus agalactiae.*

EXAMPLE II

The following formulation was prepared:
Chlorhexidine—2.5 gm
PVP K30—1.25 gm
Isopropanol 40%—200 ml.
Glycerine—22.5 ml.
Sorbitol 70%—16 ml.
Citric Acid—0.093 gm
Sodium Citrate—0.026 gm
FD & C. Blue No. 1—0.0937 gm
Water q. s.—500 ml.

The formulation was prepared by dissolving the chlorhexidine in the isopropanol and then dissolving the PVP in that solution. The glycerine was then added to the solution. The citric acid and sodium citrate were dissolved in water and the sorbitol was added thereto. All were then mixed with sufficient water to 500 ml.

In a comparable test procedure, the results were similar to that of Example I.

EXAMPLE III

The following emulsion formulation was prepared:
Triclosan—2.5 gm
PVP K30—2.5 gm
Volpo No. 10—15 gm
Crodamul—25 gm
Triethanolamine—1.25 gm
Isopropanol—200 ml.
Glycerine—22.5 ml.
Sorbitol 70%—16 ml.
Carbopol No. 941 2%—62.5 gm
FD & C Yellow No. 6—0.0937 gm
Water q. s.—500 ml.

The formulation was prepared by dissolving the Triclosan in the isopropanol and then dissolving the PVP therein. The Volpo, Crodamul and triethanolamine were added and dissolved. To a water solution of Carbopol and color was added and dissolved the glycerine and sorbitol. The water and the alcohol were mixed in a Lightin mixer until an emulsion was formed.

In a comparable test procedure, the results were similar to that of Example I.

What is claimed is:

1. An antimicrobial animal teat dip tincture composition consisting essentially of the ingredients of:
   (a) a water-soluble lower alkanol microbicide in an amount of 15 to 70%;
   (b) a water and lower alkanol-soluble film-forming polymer in an amount of 0.1 to 15%;
   (c) a water-soluble emollient in an amount of 0.1 to 10%;
   (d) water
wherein the composition provides a fast acting microbicidal teat dip which does not cause substantial irritation of the teats with repeated use thereof and may be washed from the teats with water.

2. The composition of claim 1, which in addition also contains a water-soluble dye.

3. The composition of claim 1, which in addition also contains a buffer for controlling the pH of the composition between 4 and 7.

4. The composition of claim 1, which in addition also contains a sequestering agent for preventing precipitation of any of the said ingredients in hard water.

5. The composition of claim 1, wherein the alkanol has 3 carbon atoms or less.

6. The composition of claim 5, wherein the alkanol is saturated.

7. The composition of claim 1, wherein the polymer is a vinyl polymer, a natural gum polymer or gelatin.

8. The composition of claim 7, wherein the polymer is polyvinylpyrrilodone.

9. The composition of claim 1, wherein the emollient is a polyhydric alcohol.

10. The composition of claim 9, wherein the polyhydric alcohol is glycerol or sorbitol.

11. The composition of claim 1, wherein the composition in addition also contains a further water/alcohol-soluble microbicide.

12. The composition of claim 11, wherein the further soluble microbicide is a quaternary ammonium compound.

13. The composition of claim 11, wherein the soluble microbicide is selected from the group consisting of cetyl pyridinum chloride and N-alkyl-dimethyl-benzyl ammonium chloride.

14. The composition of claim 13, wherein the soluble microbicide is cetyl pyridinum chloride.

15. The composition of claim 1, wherein the composition in addition also contains a further water/alcohol-insoluble mircobicide.

16. The composition of claim 15, wherein the insoluble microbicide is a phenolic microbicide.

17. The composition of claim 15, wherein the composition in addition also contains 0.01 to 10% of an emulsifier.

18. A method for preventing mastitis in the teats of mammals comprising applying to the teats the composition of claim 1 and allowing the composition to dry on said teats so as to form a film of the polymer containing the emollient.

19. The method of claim 18, wherein the composition in addition also contains a water-soluble dye which is contained in the resulting polymer film and the teat dip composition is reapplied to the teats when no dye is visible on the treated teats.

20. The method of claim 18, wherein the composition in addition contains a buffer for controlling the pH of the composition between 4 and 7 to prevent unconfortable application of the teat dip.

21. The method of claim 18, wherein the composition in addition also contains a sequestering agent for preventing precipitation of any of the said ingredients in hard water.

22. The method of claim 18, wherein the alkanol has 3 carbon atoms or less.

23. The method of claim 18, wherein the film-forming polymer is polyvinylpyrrilodone.

24. The method of claim 18, wherein the emollient is a polyhydric alcohol.

25. The method of claim 24, wherein the polyhydric alcohol is glycerol or sorbitol.

26. The method of claim 18, wherein the composition in addition contains a further water/alcohol soluble microbicide whereby the further microbicide remains in the dried polymer film and provides residual long term mastitis protection.

27. The method of claim 26, wherein the soluble microbicide is a quaternary ammonium compound.

28. The method of claim 27, wherein the soluble microbicide is selected from the group consisting of cetyl pyridinum chloride and N-alkyl-dimethyl-benzyl ammonium chloride.

29. The method of claim 28, wherein the soluble microbicide is cetyl pyridinum chloride.

30. The method of claim 18, wherein the composition in addition also contains a further water/alcohol insoluble microbicide.

31. The method of claim 30, wherein the insoluble microbicide is a phenolic microbicide.

32. The method of claim 30, wherein said composition in addition also contains 0.01 to 10% of an emulsifier.

* * * * *